United States Patent
Gilbert et al.

(12)

(10) Patent No.: US 6,221,394 B1
(45) Date of Patent: Apr. 24, 2001

(54) DOSAGE FORMS

(75) Inventors: Julian Clive Gilbert; Andrew John McGlashan Richards; Hazel Judith Bardsley, all of Cambridge (GB)

(73) Assignee: Darwin Discovery, Ltd. (GB)

(*) Notice: Subject to any disclaimer, the term of this patent is extended or adjusted under 35 U.S.C. 154(b) by 0 days.

(21) Appl. No.: 09/478,177

(22) Filed: Jan. 5, 2000

Related U.S. Application Data

(63) Continuation of application No. 09/038,873, filed on Mar. 11, 1998.

(30) Foreign Application Priority Data

Mar. 11, 1997 (GB) .................................................. 9704978
Sep. 10, 1997 (GB) .................................................. 9719261

(51) Int. Cl.[7] .............................. H61K 9/24; H61K 9/14; H61K 9/48; H61K 9/70
(52) U.S. Cl. .................... 424/473; 424/489; 424/451; 424/472; 424/449; 424/426; 424/45
(58) Field of Search .................... 424/473, 464, 424/465, 472, 489, 45, 451, 449, 426

(56) References Cited

U.S. PATENT DOCUMENTS 5,204,116 * 4/1993 Edgren e al. .................... 424/473

FOREIGN PATENT DOCUMENTS

624366 * 11/1994 (EP) .
9600075 * 1/1996 (WO) .

* cited by examiner

*Primary Examiner*—Thurman K. Page
*Assistant Examiner*—Blessing Fubara
(74) *Attorney, Agent, or Firm*—Saliwanchik, Lloyd & Saliwanchik

(57) ABSTRACT

A pharmaceutical dosage form comprises, in one portion thereof, a substantially single (+)-enantiomer of a chiral drug other than verapamil and, in another, separate portion thereof, a substantially single (−)-enantiomer of the drug wherein, in use, the different enantiomers are released at different rates from the dosage form. The dosage form is useful for administration of chiral drugs where both enantiomers have a valid pharmacological input, and where a clinical benefit may be realised by controlling the release rates of those enantiomers. Examples of such drugs include, in particular, tramadol and warfarin.

28 Claims, 2 Drawing Sheets

DOSAGE FORMS

CROSS-REFERENCE TO A RELATED APPLICATION

This application is a continuation of co-pending application U.S. Ser. No. 09/038,873, filed Mar. 11, 1998. .

FIELD OF THE INVENTION

This invention relates to the discovery of novel pharmaceutical dosage forms of chiral drugs.

BACKGROUND TO THE INVENTION

The separate enantiomers of some chiral drugs have different therapeutic properties, and/or mechanisms of action and yet in some cases it may still be desirable to dose both enantiomers together. However, where the pharmacokinetic properties of the separate enantiomers are different, for instance due to differences in the rates at which they are metabolised, the ratio of the different enantiomers changes with time after initial dosing, which can lead to reduced efficacy of the drug. The actual enantiomeric ratio at any one time may be dependent upon a number of factors, and may be further complicated if different dosage forms provide different enantiomeric ratios. Effects such as these have been observed with the different enantiomers of Verapamil, for instance see Longstreth, J. A. Clin. Pharmacol. (1993) 18 (2nd Edition): 315–336 and Gupta et al., Eur. J. Pharm. Biopharm. (1996) 42(1): 74–81.

SUMMARY OF THE INVENTION

According to the present invention, a pharmaceutical dosage form comprises, in one portion thereof, a substantially single (+)-enantiomer of a chiral drug other than verapamil and , in another, separate, portion thereof, a substantially single (−)-enantiomer of the drug, wherein, in use, the different enantiomers are released at different rates from the dosage form.

Where the different enantiomers of the chiral drug are absorbed, metabolised, distributed or secreted by the body at different rates, their rates of release from the dosage form may be arranged such that their initial ratio, whether this is 50:50 or a non-racemic ratio, is maintained, ideally throughout the dosing period. By manipulating the administration of the different enantiomers in this way, presentation of the desired enantiomer to the target organ is optimised, thereby increasing the clinical efficacy of the drug throughout the dosing period.

The present invention may also be beneficial in administering chiral drugs whose individual enantiomers have different efficacies, different modes of action, different selectivities, e.g. to receptors or enzymes, or different toxicities.

The present invention may also be beneficial in administering chiral drugs which have a side effect associated therewith, but where the side effect resides in only one of the drug's two individual enantiomers. In this case, it may be desirable to have a different release rate for the enantiomer causing the side effect, although this will depend upon the nature of the side effect.

Examples of chiral drugs where both enantiomers have a valid pharmacological input, and where a clinical benefit may be realised by controlling the release rates of those enantiomers, include warfarin, tramadol, mianserin, carvedilol, citalopram, dobutamine, aminoglutethimide, alfuzosin, celiprolol, cisapride, disopyramide, fenoldopam, flecainide, hydroxychloroquine, ifosfamide, labetolol, mexiletine, propafenone, tegafur, terazosin, thioctic acid, thiopental and zacopride, and in particular warfarin and tramadol, and most particularly tramadol.

DESCRIPTION OF THE INVENTION

Figure 1:
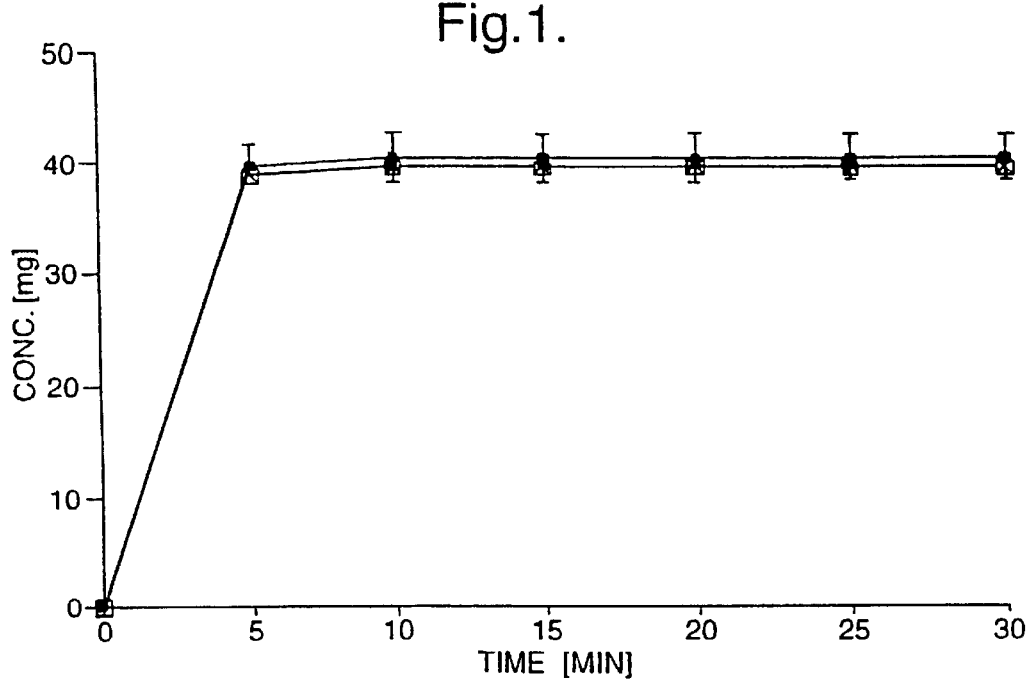
FIG. 1 is a graph of concentration of the individual enantiomers of tramadol hydrochloride released with time from the immediate-release tablets prepared in accordance with Example 1.

The present invention covers any dosage form in which the two enantiomers of a chiral drug are physically separated, or compartmentalised, so as to achieve different release rates of the different enantiomers. Such separation, or compartmentalisation, may be on a macro-scale, for instance with the different enantiomers being incorporated into separate dosage forms for simultaneous or sequential administration, i.e. as a kit, or separation of the different enantiomers may be on a micro-scale, for instance with the different enantiomers being present within the same dosage form and despite their physical separation being intimately mixed, or somewhere intermediate the two.

In the context of this Application, by substantially single enantiomer typically we means that one enantiomer is in an excess of at least 70% by weight with respect to the other enantiomer, and is preferably in an excess of at least 80%, and more preferably 90%, or higher. Furthermore, by a non-racemic ratio of enantiomers typically we mean that both enantiomers are present, with either the (−)-enantiomer being present in an amount in excess of that of the (+)-enantiomer, or vice versa.

A number of release profiles for the different enantiomers of a chiral drug may be realised by way of he dosage forms of the present invention. For instance, a dosage form may be designed to allow immediate release of one enantiomer and sustained, or controlled, release of the other enantiomer. In this case, by immediate release typically we mean that release of the respective enantiomer occurs substantially immediately or after only a short delay, usually no more than five to ten minutes, after administration of the dosage form, and continues usually over a period of up to one to two hours. By sustained, or controlled, release typically we mean that release of the respective enantiomer is delayed usually for at least one hour and frequently longer, for instance for two or more hours, after administration of the dosage form. The sustained, or controlled, release may be constant or variable throughout the treatment period.

The dosage forms of the present invention may be designed to release either of the enantiomers faster than the other, or before the other, depending upon the condition to be treated, or the patient type. It may be desirable to maintain a constant ratio of the separate enantiomers at the target tissue over a specified period of time, for instance at least 8 hours a day, preferably at least 12 hours a day, most preferably 24 hours a day. The ratio maintained may be 50:50, or a non-racemic ratio in which either the amount of the (+)-enantiomer is greater than the (−)-enantiomer, or vice versa.

Another option would be to vary the ratio of the two enantiomers throughout the treatment period, or at least for a portion of that period. For instance, the release rate of either or both enantiomers can be arranged to vary, so that either the relative proportion of the (+)-enantiomer or of the (−)-enantiomer increases, or decreases, with time. The latter may be achieved, for instance, by using a number of different release coatings for the respective enantiomer.

As mentioned above, the present invention may have particular application in the administration of tramadol and warfarin. Tramadol is formulated as the racemate for use as a high-potency analgesic with opioid-like properties. The analgesic efficacy and safety of the racemate and the individual enantiomers have been investigated in a randomised, double-blind study with gynaecological patients using intravenous patient-controlled analgesia (see Grond, S, et al. Pain (1995) 62(3):313–320). Although (+)-tramadol appeared to be more potent in producing analgesia, it also produced more nausea and vomiting. Since the racemate has more efficacy than (−)-tramadol and no more side effects than (+)-tramadol, the authors concluded that the racemate had more clinical utility. In another study it was shown that there is complementary and synergistic antinociceptive interaction between the individual enantiomers of tramadol (see Raffa, R. B. et al. J Pharmacol. Exp. Ther. (1993) 267(1): 331–340). The enantiomers have different potencies at opioid receptors, and in inhibiting serotonin re-uptake and noradrenaline re-uptake. It therefore appears that both enantiomers of tramadol contribute to the analgesic effect. Thus, it is possible that controlled administration of the individual enantiomers at different rates, facilitated by the dosage form embodied by the present invention, could result in even more useful analgesia without additional side effects.

A preferred dosage form for administration of tramadol is one in which (−)-tramadol is in immediate-release form and (+)-tramadol is in a sustained-, or controlled-, release form. In this case, the release rate of the (+)-enantiomer could be controlled in such a way to reduce the adverse side effects of nausea and/or dizziness believed to be associated with that enantiomer.

In the case of the anticoagulant drug warfarin, which is currently formulated as the racemate for clinical use, both the (S)-(−)- and (R)-(+)-enantiomers exhibit the desired hypoprothrombinemic activity, with (S)-warfarin being the more potent (see Hyneck, M. et al, Chirality in Drug Design and Synthesis (1990), p. 17–18, ed. C. Brown, Academic Press, London). However, use of warfarin in this form, i.e. as the racemate, is complicated by a delay of a few days before the onset of the desired anticoagulant effect. Thus, once therapy has commenced, careful monitoring is necessary to strike a balance between underdosing and overdosing; overdosing may lead to haemorrhage and may sometimes be fatal. This effect may be attributable to the individual enantiomers of warfarin having different affinities for albumin binding, and their being metabolised by different pathways which in turn will influence relative clearance rates. Thus, administration of separate formulations of the individual enantiomers, or a simple formulation in which the individual enantiomers are separated, may achieve a more controllable treatment regime.

A number of different types of dosage form can be envisaged, for administration by a variety of routes, e.g. oral, rectal, transdermal, nasal, opthalmic, pulmonary and injectable (subcutaneous or intravenous).

The Applicant's co-pending Application WO 97/33570, describes dosage forms from which the individual enantiomers of verapamil are released at different rates, and any of these may be employed with any of the above drugs.

For instance, one type of dosage form comprises a capsule containing two sets of multiparticulates having different release rates, one set containing the (+)-enantiomer and the other set containing the (−)-enantiomer. The multiparticulates themselves can be made by any of the conventional methods, including extrusion spheronisation, high shear granulation, non-pareil seeds, etc. The rates at which the different enantiomers are released from the multiparticulates can be achieved using any conventional controlled-release mechanism, for instance, matrix (ie. erosion diffusion), coating, or osmotic. Dosage forms of this type are suitable for oral and rectal use.

Another type of dosage form comprises two tablets, i.e. as a combined product (kit), one tablet containing the (+)-enantiomer and the other tablet containing the (−)-enantiomer, the two tablets having different release rates. Again, conventional control-release technology can be used to achieve the desired effect. For example, two tablets having different release coatings or matrices may be used, or two osmotic pump tablets having different pumping rates. The tablets can then be administered in sequence, or they can be filled into a capsule for dosing simultaneously.

Another type of dosage form comprises an osmotic pump tablet comprising two distinct portions, typically two layers, one portion containing and pumping the (+)-enantiomer at one rate, and the other portion containing and pumping the (−)-enantiomer at another rate.

Another type of dosage form comprises a bi-layered tablet, one layer containing the (+)-enantiomer and the other layer containing the (−)-enantiomer, the two layers having different release rates for their respective enantiomers. Again, conventional control-release technology can be used to achieve the desired effect.

One example of a bi-layered tablet may have (−)-tramadol in an outer layer as a starter treatment, leading on to release of (+)-tramadol from the core which would provide maintenance therapy. Another example of a bilayered tablet may have (S)-warfarin in an outer layer as a starter treatment, and (R)-tramadol in a core for maintenance therapy. Different percentages of the individual enantiomers could be used in different tablet preparations so that doses could be titrated for individuals.

Another type of dosage form comprises a compressed coat tablet having a core containing one of the (+)- and (−)-enantiomers and, surrounding the core, a shell containing the other of the (+)- and (−)-enantiomers, the core and shell having different release rates for their respective enantiomers.

Another type of dosage form comprises a patch for placing adjacent a patient's skin, the patch comprising two distinct portions, one portion containing the (+)-enantiomer and the other portion containing the (−)-enantiomer, the two portions having different release rates for their respective enantiomers. Alternatively, two separate patches may be used, i.e. as a combined product (kit), one patch containing the (+)-enantiomer and the other patch containing the (−)-enantiomer, the two patches having different release rates.

Another type of dosage form comprises a polymer implant comprising two distinct portions, one portion containing the (+)-enantiomer and the other portion containing the (−)-enantiomer, the two portions having different release rates for their respective enantiomers. Alternatively, two separate polymer implants may be used, i.e. as a combined product (kit), one implant containing the (+)-enantiomer and the other implant containing the (−)-enantiomer, the two implants having different release rates.

Another type of dosage form comprises an aerosol containing two sets of microparticles having different release rates, one set containing the (+)-enantiomer and the other set containing the (−)-enantiomer. Alternatively, two separate aerosols may be used, one for each enantiomer, i.e. as a combined product (kit), the microparticles of each aerosol having different release rates.

Other types of dosage form may be for administration by injection. With dosage forms of this type, different release rates of the different enantiomers may be achieved by means of, for example, liposomes or microparticulates.

As, in the present invention, the two enantiomers are effectively dosed separately, it is essential that they are provided in a form that is not harmful to the prospective patient. If they are provided in salt form, both salts should preferably be stable and non-hygroscopic.

The dosage forms of the present invention can be used in the treatment of conditions for which the chiral drug is usually administered, particularly in patients disposed to, or who may be put at risk by exposure to, an adverse side effect.

The present invention is now illustrated by way of the following Examples.

EXAMPLES

IN the following, tablets were prepared using a Universal Testing Instrument (Instron floor model, Instron Limited, High Wycombe, United Kingdom) at a compression rate of 1 mm/min, using a tabletting pressure of 200 MPa, and an 8 mm flat-faced punch.

The disintegration properties of the tablets were assessed in a disintegration tester (Erweka GmbH, Heusenstamm Germany) according to BP using water at 37° C. ±0.2 K. The dissolution profiles of the tablets were evaluated employing the USP XXIII paddle method (Pharmatest, Hamburg, Germany) using 1000 ml distilled water at 37° C.±0.5 K and a paddle speed of 100 rpm. The dissolved amount of drug, whether (+)- or (−)-tramadol hydrochloride, we measured with on-line UV (Phillips PU 8620, Hamburg, Germany) at a wavelength of 220 nm.

In the accompanying Figures, Figures ■ represents (+)-tramadol hydrochloride and ■ represents (−)-tramadol hydrochloride.

Example 1

Immediate-release tablets were prepared from a powder mixture of 50.0 mg (+)- or (−)-tramadol hydrochloride, 46.5 mg microcrystalline cellulose, 3.0 mg croscarmellose sodium and 0.5 mg magnesium stearate, using a tabletting pressure of 200 MPa. Disintegration was monitored over 30 minutes.

The drug release from the immediate-release tablets is depicted in FIG. 1, with the y-axis showing the concentrations of the individual enantiomers in the dissolution medium. The dissolution pattern observed guarantees a rapid pharmaceutical availability of the drug.

Example 2

Controlled-release tablets were prepared from a powder mixture of 50.00 mg (+)- or (−)-tramadol hydrochloride, 119.15 mg hydroxypropyl methyl cellulose (HPMC) and 0.85 mg magnesium stearate, using a tabletting pressure of 200 MPa. Disintegration was monitored over a period of 7 hours.

Figure 2:
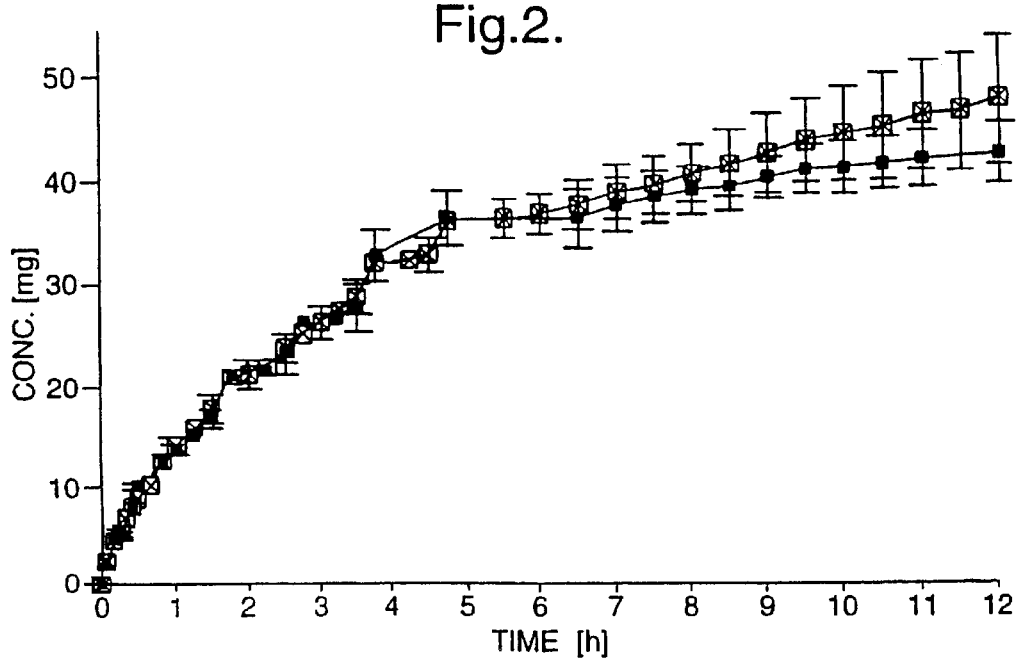
FIG. 2 is a graph of concentration of the individual enantiomers of tramadol hydrochloride released with time from the controlled-release tablets prepared in accordance with Example 2.
Figure 3:
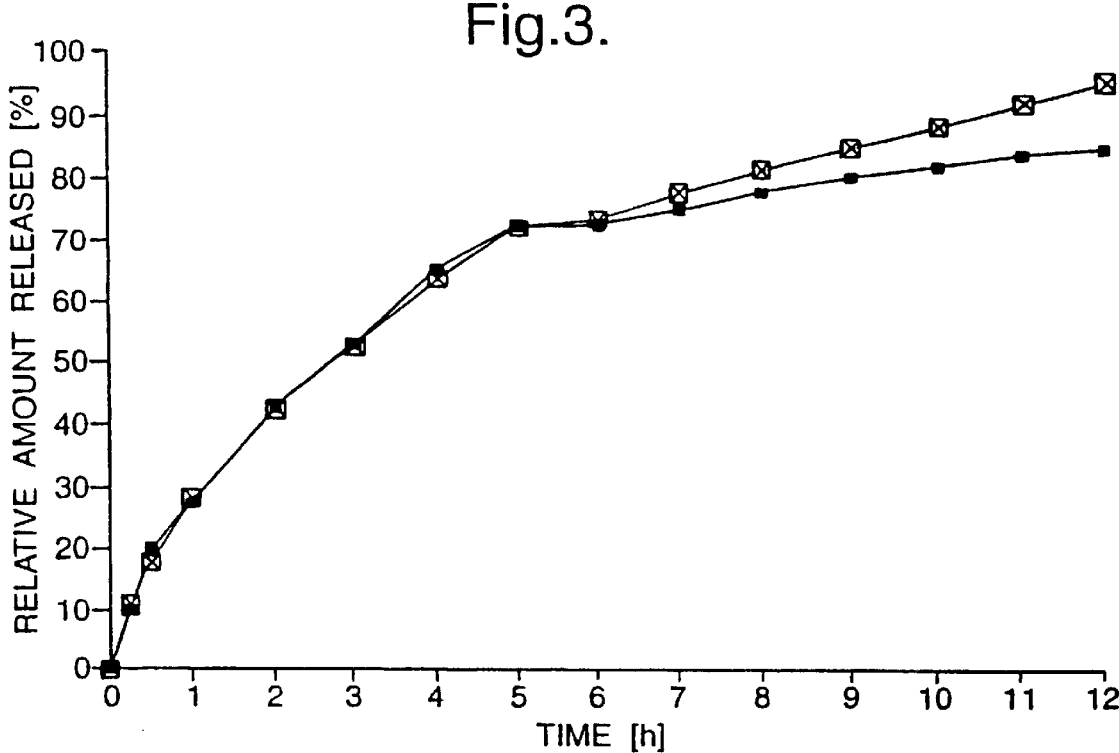
FIG. 3 is a graph of percentage release of the individual enantiomers of tramadol hydrochloride with time from the controlled-release tablets prepared in accordance with Example 2.

The drug release of the controlled-release tablets is depicted in FIG. 2, as a dissolution profile, with the y-axis showing the concentrations of the individual enantiomers in the dissolution medium, and in FIG. 3 as a percentage of drug release. A twelve hour controlled-release was achieved with the present formulation. After 6 hours, the (−)-enantiomer is releases slightly faster than the (+)-enantiomer, achieving nearly 100% drug release at 12 hours, whereas only 86% of the (+)-enantiomer was released after 12 hours. Below 6 ours, the drug release profiles of the two enantiomers were very similar.

Example 3

Bi-layered tablets were prepared by pre-compressing the powder mixture of Example 2 at a tabletting pressure of 20 MPa to form a controlled-release layer. The powder mixture of Example 1, containing the opposite enantiomer of tramadol hydrochloride to that used in the controlled-release layer, was then filled on top of the controlled-release layer, and the whole tablet compressed using a tabletting pressure of 200 MPa.

Figure 4:
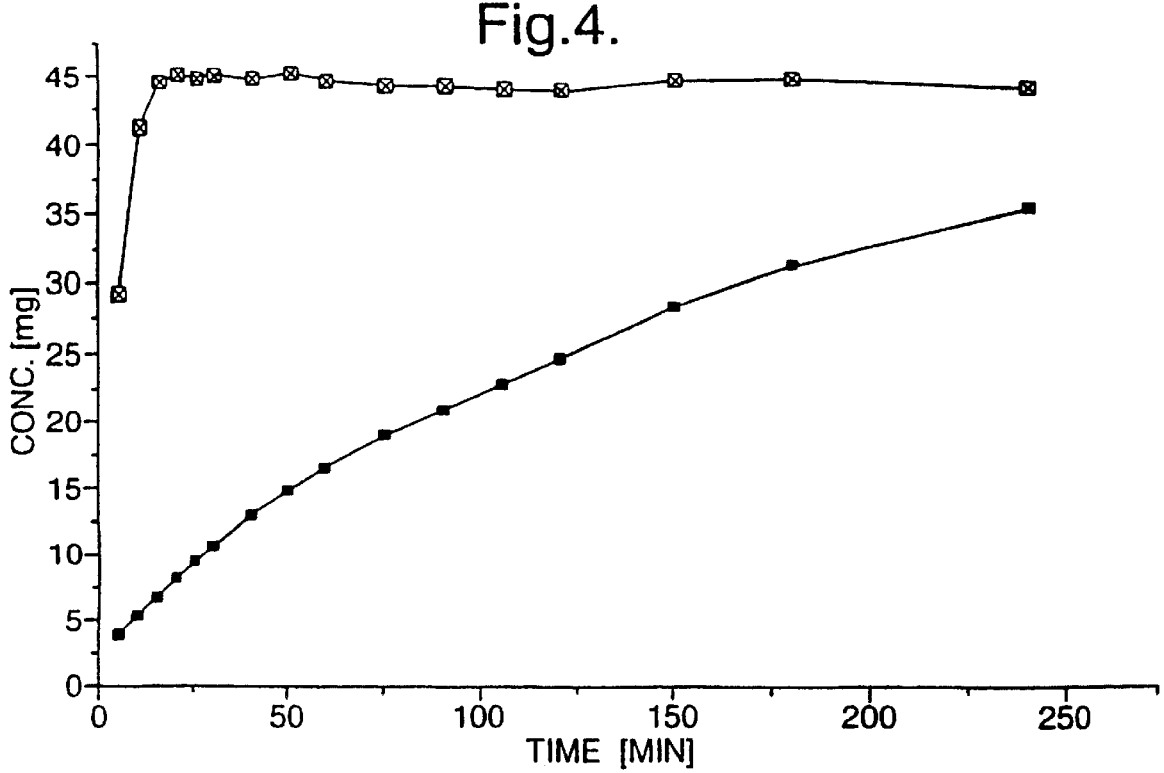
FIG. 4 is a graph of concentration of tramadol free base released with time from the bilayered tablets prepared in accordance with Example 3.

The dissolution profiles of the individual layers of the bi-layered tablets were obtained by chiral HPLC analysis of tramadol free base using a Chiralpak AD Column (eluent 90% heptane, 9.99% isopropanol, 0.01% diethylamine), on which (+)-tramadol had a retention time of 4.5 minutes and (−)-tramadol a retention time of 5.6 minutes, and are depicted in FIG. 4, in which the y-axis shows the concentration of the individual enantiomers in the dissolution medium.

Shorter release profiles from a controlled-release layer may be achieved simply by altering the amount of the excipients used, and in the present case by lowering the amount of HPMC. Furthermore, if increased dosage is required, the table diameter may be increased.

What is claimed is:

1. A pharmaceutical dosage form comprising, in one portion thereof, substantially single (+)-tramadol, wherein said (+)-tramadol is in an excess of at least 70% by weight with respect to (−)-tramadol, and, in another, separate portion thereof, substantially single (−)-tramadol, wherein said (−)-tramadol is in an excess of at least 70% by weight with respect to (+)-tramadol, and wherein, in use, the different tramadol enantiomers are released at different rates from the dosage form.

2. The dosage form, according to claim 1, wherein said release rates of said different tramadol enantiomers are selected to give a substantially constant ratio of those enantiomers at a target tissue for at least about 8 hours.

3. The dosage form, according to claim 2, wherein the ratio of said tramadol enantiomers at said target tissue is about 50:50.

4. The dosage form, according to claim 2, wherein the ratio of said tramadol enantiomers at said target tissue is a non-racemic ratio, with (+)-tramadol in excess compared with (−)-tramadol.

5. The dosage form, according to claim 2, wherein the ratio of said tramadol enantiomers at said target tissue is a non-racemic ratio, with (−)-tramadol in excess compared with (+)-tramadol.

6. The dosage form, according to claim 1, wherein said release rate of one of said enantiomers varies with time.

7. The dosage form, according to claim 6, wherein said rate of release of (+)-tramadol increases or decreases with time.

8. The dosage form, according to claim 6, wherein said rate of release of (−)-tramadol increases or decreases with time.

9. The dosage form, according to claim 1, from which the (+)-tramadol is released faster than the (−)-tramadol.

10. The dosage form, according to claim 1, from which (−)-tramadol is released faster than the (+)-tramadol.

11. The dosage form, according to claim 1, wherein one enantiomer is in immediate release form and the other enantiomer is in sustained release form.

12. The dosage form, according to claim 1, wherein (−)-tramadol is in immediate release form and (+)-tramadol is in sustained release form.

13. The dosage form, according to claim 1, which comprises a capsule containing a plurality of first particles containing (−)-tramadol and a plurality of second particles containing (+)-tramadol, the first and second particles having different release rates for their respective enantiomers.

14. The dosage form, according to claim 1, which comprises a first tablet containing (+)-tramadol and a second table containing (−)-tramadol, the first and second tables having different release rates for their respective enantiomers.

15. The dosage form, according to claim 14, wherein said first and second tablets are enclosed within a capsule.

16. The dosage form, according to claim 1, which comprises an osmotic pump tablet having a first portion containing (+)-tramadol and a second portion comprising (−)-tramadol, wherein said first and second portions have different pumping rates for their respective enantiomers.

17. The dosage form, according to claim 1, which comprises a bi-layered tablet, one layer containing (+)-tramadol and the other containing (−)-tramadol, the two layers having different release rates for their respective enantiomers.

18. The dosage form, according to claim 1, which is a bi-layered tablet having an outer layer comprising (−)-tramadol and a core comprising (+)-tramadol.

19. The dosage form, according to claim 1, which comprises a compressed coat tablet having a core containing one of the enantiomers of tramadol and, surrounding the core, a shell containing the other of the enantiomers of tramadol.

20. The dosage form, according to claim 1, which comprises a patch for placing adjacent a patient's skin, said patch comprising a first portion containing the (+)-tramadol and a second portion containing (−)-tramadol, the first and second portions having different release rates for their respective enantiomers.

21. The dosage form, according to claim 1, which comprises two patches, each for placing adjacent a patient's skin, one patch containing the (+)-tramadol and the other patch containing the (−)-tramadol, said two patches having different release rates.

22. The dosage form, according to claim 1, which comprises a polymer implant having a first portion containing the (+)-tramadol and a second portion containing the (−)-tramadol, wherein said first and second portions have different release rates for their respective enantiomers.

23. The dosage form, according to claim 1, which comprises two polymer implants, one implant containing (+)-tramadol and the other implant containing (−)-tramadol, said two implants having different release rates.

24. The dosage form, according to claim 1, which comprises an aerosol containing two sets of microparticles having different release rates, one set containing the (+)-tramadol and the other set containing the (−)-tramadol.

25. The dosage form, according to claim 1, which comprises two aerosols, one containing microparticles containing (+)-tramadol and the other containing microparticles containing (−)-tramadol, the microparticles in the two aerosols having different release rates for their respective enantiomers.

26. A pharmaceutical dosage form comprising, in one portion thereof, substantially single (+)-tramadol, wherein said (+)-tramadol is in excess of at least 70% by weight with respect to (−)-tramadol, and, in another, separate portion thereof, substantially single (−)-tramadol, wherein said (−)-tramadol is in excess of at least 70% by weight with respect to (+)-tramadol, and wherein the different tramadol enantiomers are released sequentially from the dosage form.

27. A method of providing analgesia, comprising administering to a patient the substantially single enantiomers of tramadol in a dosage form as defined in claim 1.

28. A method of providing analgesia, comprising administering to a patient the substantially single enantiomers of tramadol in a dosage form as defined in claim 25.

* * * * *

UNITED STATES PATENT AND TRADEMARK OFFICE
CERTIFICATE OF CORRECTION

PATENT NO.   : 6,221,394 B1
DATED        : April 24, 2001
INVENTOR(S)  : Julian Clive Gilbert, Andrew John McGlashan Richards, Hazel Judith Bardsley It is certified that error appears in the above-identified patent and that said Letters Patent is hereby corrected as shown below:

Column 7,
Line 24, "tables" should read -- tablets --.

Signed and Sealed this

Eighteenth Day of December, 2001

Attest:

JAMES E. ROGAN
*Attesting Officer*        *Director of the United States Patent and Trademark Office*